(12) United States Patent
Zhao et al.

(10) Patent No.: US 10,765,675 B2
(45) Date of Patent: Sep. 8, 2020

(54) COMPOSITIONS AND METHODS FOR TREATING EWING FAMILY TUMORS

(71) Applicant: The Methodist Hospital, Houston, TX (US)

(72) Inventors: Hong Zhao, Missouri City, TX (US); Stephen T. C. Wong, Houston, TX (US)

(73) Assignee: The Methodist Hospital, Houston, TX (US)

( * ) Notice: Subject to any disclaimer, the term of this patent is extended or adjusted under 35 U.S.C. 154(b) by 0 days.

(21) Appl. No.: 15/755,258

(22) PCT Filed: Aug. 22, 2016

(86) PCT No.: PCT/US2016/047984
§ 371 (c)(1),
(2) Date: Feb. 26, 2018

(87) PCT Pub. No.: WO2017/035057
PCT Pub. Date: Mar. 2, 2017

(65) Prior Publication Data
US 2018/0243299 A1    Aug. 30, 2018

Related U.S. Application Data

(60) Provisional application No. 62/209,645, filed on Aug. 25, 2015, provisional application No. 62/209,197, filed on Aug. 24, 2015.

(51) Int. Cl.
*A61K 31/506* (2006.01)
*A61P 35/00* (2006.01)
*A61K 31/155* (2006.01)
*A61K 45/06* (2006.01)
*C12Q 1/6886* (2018.01)

(52) U.S. Cl.
CPC .......... *A61K 31/506* (2013.01); *A61K 31/155* (2013.01); *A61K 45/06* (2013.01); *A61P 35/00* (2018.01); *C12Q 1/6886* (2013.01); *C12Q 2600/158* (2013.01)

(58) Field of Classification Search
CPC combination set(s) only.
See application file for complete search history.

(56) References Cited

U.S. PATENT DOCUMENTS

2009/0227464 A1   9/2009   Avigad et al.
2013/0035329 A1   2/2013   Saunders et al.
2013/0183281 A1   7/2013   Su et al.

FOREIGN PATENT DOCUMENTS

WO   WO-2008/089034 A2   7/2008
WO   WO-2015/013579 A1   1/2015

OTHER PUBLICATIONS

Lissat et al., Targeted Therapy in Ewing Sarcoma, 2012, ISRN Oncology, pp. 1-9 (Year: 2012).*
Chao et al "Phase II Clinical Trial of Imatinib Mesylate in Therapy of KIT and/or PDGFRα-Expressing Ewing Sarcoma Family of Tumors and Desmoplastic Small Round Cell Tumors" Anticancer Research vol. 30, pp. 547-552, 2010.
Curvello et al "Metformin Promotes Cancer Cells Death, Inhibits PGP Expression and Sensitize MDR Leukemic Cells to the Effects of Imatinib Mesylate" Annals of Oncology vol. 24, pp. 123-126, 2013.
Garofalo et al "Metformin as an Adjuvant Drug Against Pediatric Sarcomas: Hypoxia Limits Therapeutic Effects of the Drug" PLOS ONE vol. 8, pp. 1-12, 2013.

* cited by examiner

*Primary Examiner* — Kortney L. Klinkel
*Assistant Examiner* — Tori Strong
(74) *Attorney, Agent, or Firm* — Cesari & McKenna, LLP

(57) ABSTRACT

A method for treating a sarcoma by administering a tyrosine kinase inhibitor and a biguanide compound. Also described is a method for treating a tumor of the Ewing Sarcoma family by obtaining a tumor sample; determining in the sample gene expression levels of ACTB, B2M, MLH1, PRKDC, XPC, APEX1, ERCC5, MMS19, or RAD23; and administering a tyrosine kinase inhibitor and a biguanide compound. Furthermore, a pharmaceutical composition for treating a Ewing family tumor is disclosed. The composition contains a tyrosine kinase inhibitor, a biguanide compound, and a pharmaceutically acceptable excipient.

8 Claims, 4 Drawing Sheets

COMPOSITIONS AND METHODS FOR TREATING EWING FAMILY TUMORS

CROSS-REFERENCE TO RELATED APPLICATIONS

The present application is the National Stage of International Application No. PCT/US2016/047984, filed on Aug. 22, 2016, which claims the benefit of U.S. Provisional Patent Application Ser. No. 62/209,197 filed on Aug. 24, 2015 and U.S. Provisional Patent Application Ser. No. 62/209,645 filed on Aug. 25, 2015. The contents of these prior applications are hereby incorporated by reference in their entirety.

BACKGROUND

The Ewing family of tumors is a group of cancers that includes Ewing tumor of bone ("Ewing's sarcoma"), extraosseous Ewing tumors, primitive neuroectodermal tumors (PNET), and Askin tumors (PNET of the chest wall). These tumors are aggressive malignancies that occur mainly in the childhood through adolescent/young adult years. Over 85% of cases of Ewing family tumors result from a chromosomal translocation, which fuses the EWS gene on chromosome 22 to the FLI1 gene on chromosome 11. The EWS/FLI fusion protein functions in the pathogenesis of Ewing family of tumors by modulating the expression of target genes.

Among the Ewing family of tumors, Ewing's sarcoma is the second most common primary bone cancer affecting children and young adults and is also one of the most common soft tissue malignancies of this age group.

Despite advances in treatment of localized Ewing's sarcoma, almost all patients have asymptomatic metastatic disease at the time of diagnosis. The long-term survival for metastatic Ewing's sarcoma is less than 10%.

Doxorubicin is the current standard systemic therapy for these tumors. However, only 20% of sarcomas respond to this drug. Furthermore, the clinical utility of doxorubicin is limited by significant side-effects, in particular irreversible cardiac toxicity.

A significant unmet medical need exists for new therapeutic agents that are effective in the treatment of Ewing family tumors and lack untoward cardiac cytotoxicity.

SUMMARY

To satisfy the unmet need set forth above, a method for treating a sarcoma is provided. The method is carried out by administering to a subject having a sarcoma an effective amount of a tyrosine kinase inhibitor and an effective amount of a biguanide compound.

A method for treating a tumor of the Ewing family is also disclosed herein. The method includes (i) obtaining a tumor sample; (ii) determining in the sample an elevated level of gene expression of ACTB, B2M, MLH1, PRKDC, XPC, APEX1, ERCC5, MMS19, or RAD23 as compared to a predetermined level of expression of the gene; and (iii) administering to the subject an effective amount of a tyrosine kinase inhibitor and an effective amount of a biguanide compound.

Furthermore, a pharmaceutical composition for treating a Ewing family tumor is disclosed. The composition contains a tyrosine kinase inhibitor, a biguanide compound, and a pharmaceutically acceptable excipient.

The details of one or more embodiments of the present invention are set forth in both the drawings and description below. Other features, objects, and advantages of the invention will be apparent from the description and from the claims.

Importantly, all references cited herein are hereby incorporated by reference in their entirety.

BRIEF DESCRIPTION OF THE DRAWINGS

The invention description below refers to the accompanying drawings, of which.

DETAILED DESCRIPTION

Figure 1A:
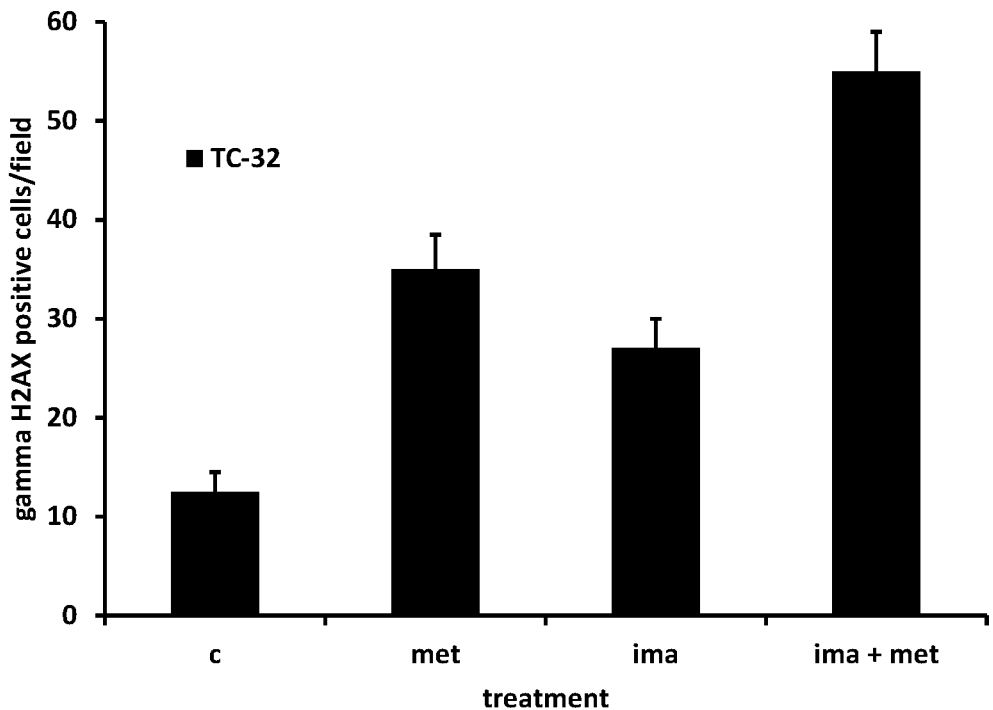
FIG. 1A is a bar graph showing the quantification of gamma histone H2AX (γ-H2AX) levels by immunofluorescence staining in TC-32 Ewing sarcoma cells treated with vehicle (c), 10 mM metformin (met), 5 μM imatinib (ima), or both drugs together (ima+met). Values are expressed as the number of γ-H2AX-positive cells per high-power field. Error bars represent standard deviation.
Figure 1B:
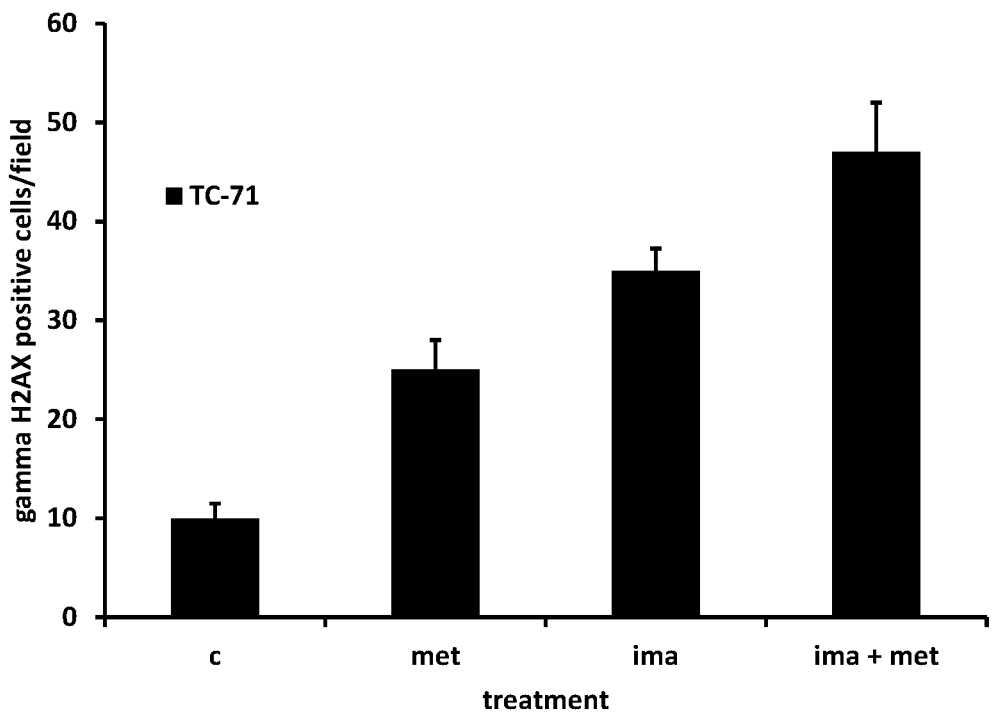
FIG. 1B is a bar graph showing the quantification of γ-H2AX levels by immunofluorescence staining in TC-71 Ewing sarcoma cells. Treatments and values are as described in the legend for FIG. 1A above. Error bars represent standard deviation.
Figure 2A:
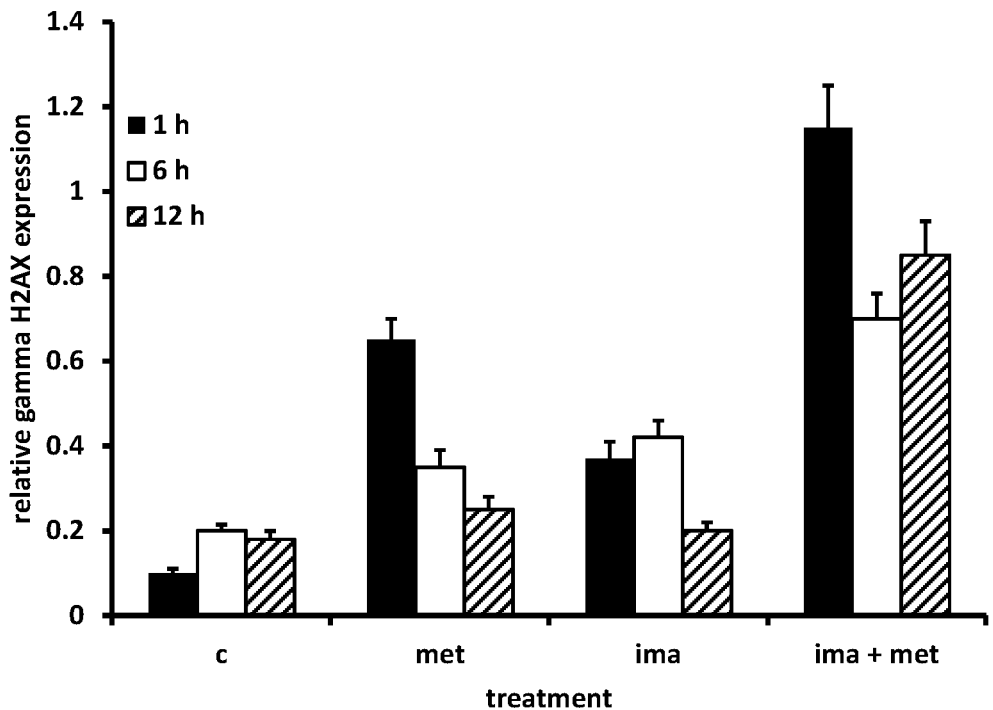
FIG. 2A is a bar graph showing relative expression of γ-H2AX in TC-32 cells either untreated (c) or treated with metformin (met), imatinib (ima), or both (ima+met) for the times indicated. Values are relative γ-H2AX expression determined by Western blot. Drug treatments are as described in the legend for FIG. 1A above. Error bars represent standard deviation.
Figure 2B:
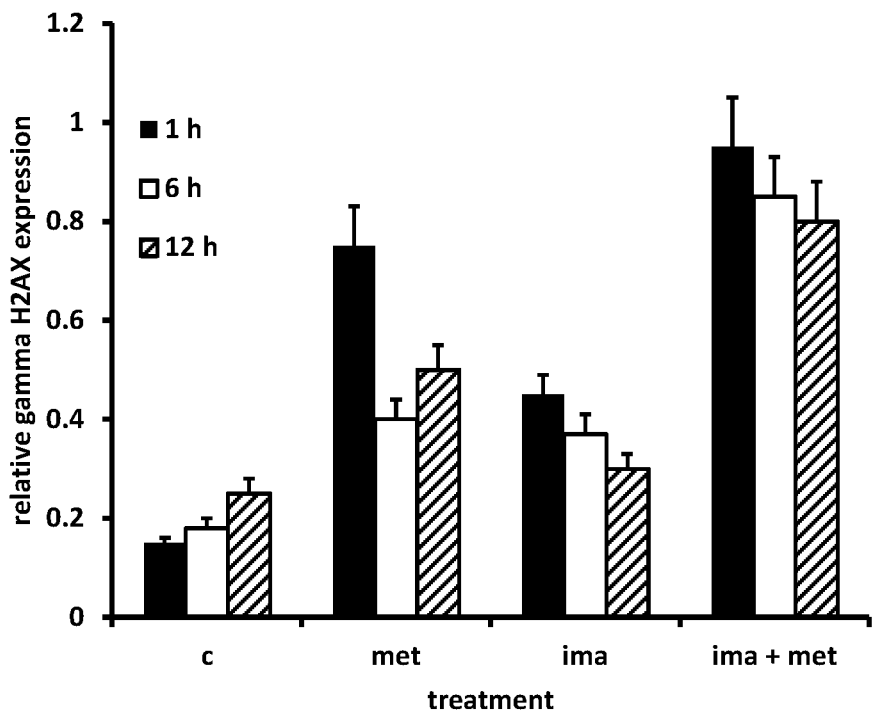
FIG. 2B is a bar graph showing relative expression of γ-H2AX in TC-71 cells treated with metformin, imatinib, or both for the times indicated. Values and drug treatments are as described in the legend for FIG. 2A above. Error bars represent standard deviation.

As mentioned above, the invention encompasses a method for treating cancer. The method includes administering to a subject having a sarcoma an effective amount of a tyrosine kinase inhibitor and an effective amount of a biguanide compound.

The tyrosine kinase inhibitor can be imatinib, dasatinib, nilotinib, sunitinib, pazopanib, quizartinib, crenolanib, or sorafenib. In a particular embodiment, the tyrosine kinase inhibitor is imatinib.

The biguanide compound can be, but is not limited to, proguanil, chlorproguanil, or metformin. In a specific method, the biguanide compound is metformin.

In a particular example, the method described, supra, also includes administering two different tyrosine kinase inhibitors. The two different tyrosine kinase inhibitors can be chosen from, e.g., imatinib, dasatinib, nilotinib, sunitinib, pazopanib, quizartinib, crenolanib, and sorafenib.

In a different example, the method includes administering two different biguanide compounds. An exemplary method includes administering two different biguanide compounds selected from proguanil, chlorproguanil, and metformin.

The method can further include administering a chemotherapy agent different from the tyrosine kinase inhibitors discussed above. Exemplary chemotherapy agents that can be administered together with the tyrosine kinase inhibitor and the biguanide compound are cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, and a topoisomerase inhibitor. Combinations of these chemotherapy agents can also be administered.

Also within the scope of the method is exposing tumor tissue to ionizing radiation in conjunction with administering the tyrosine kinase inhibitor and the biguanide compound.

The method is particularly effective for treating a Ewing family tumor. Examples of such tumors are a Ewing tumor of bone, an extraosseous Ewing tumor, a primitive neuroectodermal tumor, and an Askin tumor.

A second method effective for treating a Ewing family tumor is disclosed.

The method includes obtaining a tissue sample from a Ewing family tumor. A tissue sample can be obtained via techniques known in the art, e.g., via a needle biopsy.

Gene expression levels are determined in the sample to be elevated as compared to a predetermined level of gene expression. Not to be bound by theory, it is believed that patients have a poor clinical outcome when expression of specific genes in a Ewing family tumor is elevated as compared to expression levels of the same genes in other Ewing family tumor patients having a good clinical outcome. See Example 6, infra. A poor clinical outcome is death, metastasis, 3 year recurrence, and 5 year recurrence.

An elevated gene expression level is determined for one or more of Beta Cytoskeletal Actin (ACTB), Beta-2-Microglobulin (B2M), DNA Mismatch Repair Protein (MLH1), DNA-Dependent Protein Kinase Catalytic Subunit (PRKDC), Xeroderma Pigmentosum Complementation Group C (XPC), APEX Nuclease Multifunctional DNA Repair Enzyme (APEX1), DNA Excision Repair Protein ERCC-5 (ERCC5), Nucleotide Excision Repair Homolog MMS19 (MMS19), and UV Excision Repair Protein RAD23 Homolog A (RAD23A).

In one example, elevated gene expression levels are determined by measuring mRNA levels by quantitative polymerase chain reaction. In another example, gene expression levels are determined by hybridization of mRNA to a gene expression microarray. In yet another example, gene expression levels are measured by measuring protein levels by immunoassay.

The method includes administering a tyrosine kinase inhibitor and a biguanide compound. Appropriate tyrosine kinase inhibitors and biguanide compounds are described above. In a particular method, the tyrosine kinase inhibitor is imitanib and the biguanide compound is metformin.

Furthermore, within the scope of this method is administering two distinct tyrosine kinase inhibitors or two distinct biguanide compounds.

The method can also include administering one or more chemotherapy agents selected from cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, and a topoisomerase inhibitor.

A pharmaceutical composition is provided for treating a Ewing family tumor. The composition includes a tyrosine kinase inhibitor, a biguanide compound, and a pharmaceutically acceptable excipient.

Exemplary tyrosine kinase inhibitors are imatinib, dasatinib, nilotinib, sunitinib, pazopanib, quizartinib, crenolanib, and sorafenib.

Metformin is one biguanide compound that can be included in the composition. The biguanide compound can also be proguanil or chlorproguanil.

In particular embodiments, the pharmaceutical composition includes two different tyrosine kinase inhibitors or two different biguanide compounds.

To facilitate drug delivery, the pharmaceutical composition can further contain a delivery agent such as liposome, a surfactant, a niosome, an ethosome, a transferosome, a phospholipid, a sphingosome, a nanoparticle, a microparticle, or combinations of these agents.

In another example, the pharmaceutical composition also includes one or more of an immunomodulating agent, a neuroactive agent, an anti-inflammatory agent, an antilipidemic agent, a hormone, a receptor agonist, a receptor antagonist, an anti-infective agent, a protein, a peptide, an antibody, an antigen-binding fragment, an enzyme, an RNA, a DNA, an siRNA, an mRNA, a ribozyme, a hormone, a cofactor, a steroid, an antisense molecule, an antihypertensive agent, and a chemotherapeutic agent different from the tyrosine kinase inhibitor.

Without further elaboration, it is believed that one skilled in the art can utilize the present disclosure to its fullest extent. The following specific examples are, therefore, to be construed as merely descriptive, and not limitative of the remainder of the disclosure in any way whatsoever.

Example 1: Effect of Metformin and Imatinib on Tumor Cell Viability

The combinatorial effect of metformin and imatinib on tumor cell viability was examined on two Ewing family tumor cell lines, namely, TC-32 and TC-71. The TC-32 cell line was derived from a newly diagnosed 17 year old PNET patient and the TC-71 cell line was derived from a tumor recurrent after chemotherapy in a 22 year old Ewing's sarcoma patient. See May et al. 2013, PloS One, 8(12): e80060. Both cell lines carry the EWS/FLI gene fusion mentioned above. The breast cancer bone metastasis cell line MDA-MB231-Bo, which does not have the EWS/FLI gene fusion, and NIH 3T3 cells were used as controls.

The cells were cultured in DMEM media supplemented with 10% FBS, 1% L-glutamate, 1% sodium pyruvate, 1% penicillin/streptomycin, and 1% non-essential amino acids in a humidified atmosphere at 37° C. and in 5% $CO_2$. The ratio of cells to well surface and media volume was kept constant in all experiments.

Metformin hydrochloride and imatinib mesylate were purchased from Sigma Aldrich, and were dissolved in 0.1% DMSO prior to use.

TC-32, TC-71, MB231-Bo, and NIH 3T3 cells were plated separately in 96-well plates at a density of $1.5\times10^4$ cells per well. The cells were treated with metformin, imatinib, or with 0.1% DMSO for 24 h, followed by the addition of the CellTiter-Glo® Luminescent Cell Viability Assay reagent (Promega). Treated cells were imaged with an IVIS200 system (Xenogen Corporation, Alameda, Calif.) using the bioluminescent imaging function. An average of three kinetic bioluminescent acquisitions was obtained within 5 min Regions of interest were automatically drawn over wells and quantified with Living Image Software version 2.50.1. Data was analyzed based on total photon flux emission minus the background photon flux of blank wells.

$$CI = \frac{D_1}{D_{x1}} + \frac{D_2}{D_{x2}}$$

In this equation, $D_1$ and $D_2$ denote the doses of compound 1 and compound 2 required to have an effect of x % alone, while $D_{x1}$ and $D_{x2}$ are the doses of each respective compound needed in combination to have an effect of x %.

The CI was calculated from data obtained by testing combinations of metformin and imatinib in the cell viability assay set forth above at different concentration ratios. The interaction of these two drugs was characterized as antagonistic, defined as a CI>1.1; additive, defined as 0.9<CI<1.1; synergistic, defined as CI<0.9; and strongly synergistic, defined as CI<0.3.

The results are shown in Table 2 below.

TABLE 2

Combination index values for metformin/imatinib inhibition of tumor cell growth.

| imatinib/metformin concentration ratio | $ED_{50}$[a] | | $ED_{75}$[a] | | $ED_{90}$[a] | |
| --- | --- | --- | --- | --- | --- | --- |
| | TC-32 | TC-71 | TC-32 | TC-71 | TC-32 | TC-71 |
| 1:3000 | N.D.[b] | $1.10 \times 10^{-4}$[c] | N.D. | $2.90 \times 10^{-14}$ | N.D. | $3.10 \times 10^{-23}$ |
| 1:2000 | $1.10 \times 10^{-1}$ | $5.66 \times 10^{-7}$ | $6.37 \times 10^{-5}$ | $9.33 \times 10^{-21}$ | $3.65 \times 10^{-8}$ | $7.69 \times 10^{-34}$ |
| 1:1500 | N.D. | $1.60 \times 10^{-3}$ | N.D. | $2.97 \times 10^{-11}$ | N.D. | $3.28 \times 10^{-18}$ |
| 1:1000 | $1.22 \times 10^4$ | $1.00 \times 10^{-3}$ | $1.24 \times 10^4$ | $6.17 \times 10^{-13}$ | $1.23 \times 10^4$ | $2.74 \times 10^{-21}$ |
| 1:750 | $1.09 \times 10^5$ | $1.20 \times 10^{-4}$ | $4.78 \times 10^5$ | $2.27 \times 10^{-15}$ | $2.11 \times 10^6$ | $3.77 \times 10^{-25}$ |
| 1:500 | $9.48 \times 10^4$ | $1.40 \times 10^{-4}$ | $5.74 \times 10^5$ | $1.44 \times 10^{-15}$ | $3.50 \times 10^6$ | $1.49 \times 10^{-25}$ |
| 1:400 | $1.36 \times 10^3$ | $4.28 \times 10^{-5}$ | $1.73 \times 10^3$ | $1.54 \times 10^{-15}$ | $2.22 \times 10^3$ | $5.73 \times 10^{-25}$ |
| 1:333 | $1.26 \times 10^5$ | $2.30 \times 10^{-4}$ | $1.17 \times 10^6$ | $2.47 \times 10^{-15}$ | $1.10 \times 10^7$ | $2.82 \times 10^{-25}$ |
| 1:250 | $1.34 \times 10^{-2}$ | $1.88 \times 10^2$ | $2.60 \times 10^{-4}$ | 1.49 | $5.19 \times 10^{-6}$ | $1.26 \times 10^{-1}$ |
| 1:200 | $1.03 \times 10^4$ | $8.23 \times 10^{-5}$ | $4.68 \times 10^4$ | $2.71 \times 10^{-15}$ | $2.17 \times 10^5$ | $9.33 \times 10^{-25}$ |
| 1:100 | $7.00 \times 10^6$ | $1.20 \times 10^{-4}$ | $5.41 \times 10^8$ | $9.72 \times 10^{-15}$ | $4.32 \times 10^{10}$ | $5.81 \times 10^{-26}$ |

[a]$ED_{50}$ = effective dose that reduces cell viability by 50%, $ED_{75}$ = effective dose that reduces cell viability by 75% of cell viability, $ED_{90}$ = effective dose that reduces cell viability by 90%.
[b]N.D. = not determined.
[c]Values are the Combination Index calculated using the formula set forth above using corresponding $ED_{(50, 70, 90)}$ values for imatinib and metformin.

Three separate experiments were performed, with six replicate wells for each data point. The results are shown in Table 1 below.

TABLE 1

$EC_{50}$ of metformin and imatinib[a]

| drug | TC-32 | TC-71 |
| --- | --- | --- |
| metformin | 11.76 mM | 11.59 mM |
| | (p < 0.0001) | (p < 0.0001) |
| imatinib | 44.40 µM | 23.69 µM |
| | (p < 0.0002) | (p < 0.0001) |

[a]$EC_{50}$ is the concentration of drug that inhibits growth of the tumor cells by 50% as compared to vehicle-treated control.

Example 2: Combinatorial Effect of Metformin and Imatinib on Tumor Cell Viability The effect of metformin and imatinib mixtures at different ratios was tested using the cell viability assay described in Example 1.

The combination index (CI) accounts for the dose response of single drugs to determine the combination effect. See Chou and Talalay 1984, Adv. Enzyme Regul. 22:27-55. The equation for calculating CI is as follows:

Imatinib and metformin at a concentration ratio of 1:2000 (5 µM:10 mM) strongly synergized in killing TC-32 cells (CI<0.3). Concentrations of 5 µM and 10 mM correspond, respectively, to 11% of the $ED_{50}$ for imatinib (44.40 µM) and 85% of the $ED_{50}$ of metformin (11.76 mM) as single agents on TC-32 cells.

A synergistic effect of imatinib and metformin was observed for almost all of the concentration ratios tested on TC-71 cells. The strongest synergy was seen at imatinib:metformin concentration ratios of 1:2000 (5 µM:10 mM) and 1:3000 (5 µM:15 mM). An imatinib concentration of 5 µM is 22% of the $ED_{50}$ of this drug (23.69 µM) as a single agent on TC-71 cells. For metformin, 10 mM is 85% and 15 mM is 125% of the $ED_{50}$ of metformin (11.59 mM) as a single agent on TC-71 cells.

Imatinib and metformin, either as single agents or in combination, did not show any cytotoxicity against MB231-Bo cancer cells and 3T3 fibroblast cells at the same doses tested on the TC-32 and TC-71 cells.

Example 3: In Vitro Effect of Imatinib and Metformin on DNA Damage in Tumor Cells The levels of gamma histone H2AX (γ-H2AX), a marker for the presence of DNA double-strand breaks, were quantified in cultured TC-32 cells and TC-71 cells by immunofluorescence staining and by Western blot analysis using an anti-γ-H2AX antibody. The cells were treated as described above in Example 1 for 1, 6, and 12 h (for Western blot analysis) or for 24 h (immunofluorescence studies).

The results, shown in FIGS. 1A, 1B, 2A, and 2B, indicated that the combination of imatinib and metformin induced significantly more DNA damage as compared to either drug alone.

For example, the level of γ-H2AX expression in TC-32 cells as measured by immunofluorescence staining was twice as high after treatment of the cells with both imatinib and metformin as compared to treatment with imatinib or with metformin See FIG. 1A. Similarly, γ-H2AX expression in TC-71 cells was also elevated after treatment of the cells with both imatinib and metformin as compared to treatment with imatinib or with metformin. See FIG. 1B.

In another example, the level of γ-H2AX measured by Western blot analysis was 4-fold higher upon treating TC-32 cells with imatinib plus metformin for 12 h as compared to treating the cells with either drug individually. See FIG. 2A. Again, similar results were obtained upon drug treatment of TC-71 cells. See FIG. 2B.

Example 4: In Vivo Effect of Imatinib and Metformin on Tumor Growth

A TC-32 and a TC-71 xenograft mouse model were used to evaluate the anti-tumor effects of the combination of imatinib and metformin. $2 \times 10^6$ TC-32 or TC-71 cells in 10 μL of phosphate buffered saline were inoculated into the gastrocnemius muscle of mice. The resulting tumors were allowed to reach a minimum diameter of 0.5 cm prior to drug treatment.

The most commonly used dose of metformin is 500-1000 mg/day, resulting in plasma levels of about 1.1 mg/L, equivalent to 0.007 mM. Imatinib is commonly administered at a dose of 400-600 mg/day in adult patients, resulting in a blood concentration of about 1000 ng/mL, equivalent to 1.7 μM. The equivalent doses in mice were calculated as described in Reagan-Shaw et al. 2008, FASEB J., 22(3): 659-661. The equivalent dose of metformin in mouse is 210-420 mg/kg, and the equivalent dose of imatinib is 167-250 mg/kg. In this study, based on the in vitro results set forth in Example 2, supra, that a lower dose of each drug in combination could lead to synergistic inhibition of tumor cell growth, doses of 300 mg/kg/day metformin and 50 mg/kg/day imatinib were selected for this initial animal study.

For drug treatment, the mice were divided into four groups of 15 animals treated as follows: (i) vehicle, (ii) metformin alone at 150 mg/kg twice daily by oral gavage, (iii) imatinib alone at 50 mg/kg once daily by intraperitoneal injection, and (iv) a combination of imatinib and metformin. Both metformin and imatinib were dissolved in sterile normal saline prior to administration. Drug treatment continued for a period of two weeks. Non-invasive bioluminescent imaging was performed to monitor tumor growth every five days after initiation of treatment until Day 21.

Figure 3A:
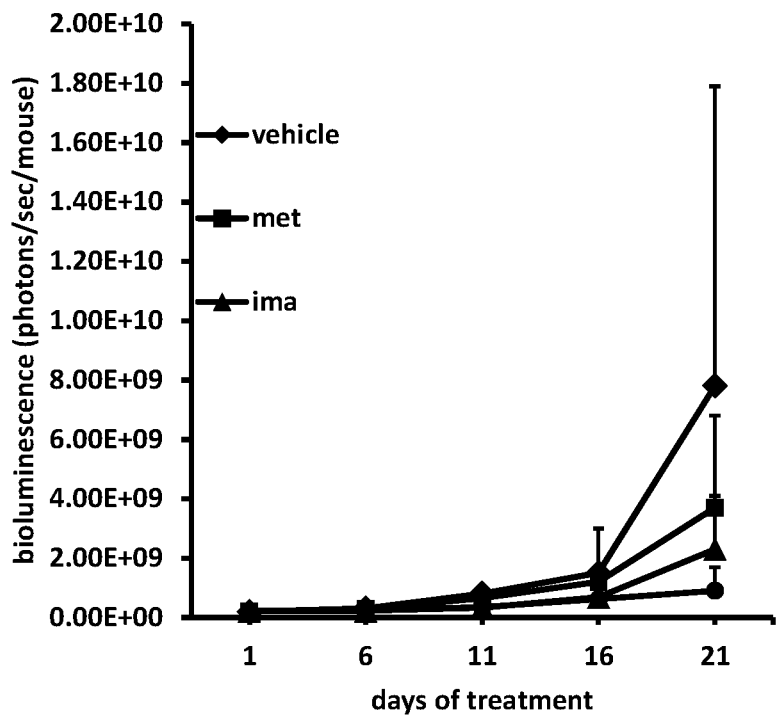
FIG. 3A is a plot of bioluminescence versus days of treatment of mice bearing TC-32 cell tumors. The mice were treated as follows: vehicle (vehicle), 150 mg/kg metformin (met), 50 mg/kg imatinib (ima), and metformin plus imatinib at the same doses (ima+met). Values are photons per second per mouse. Error bars represent standard deviation.
Figure 3B:
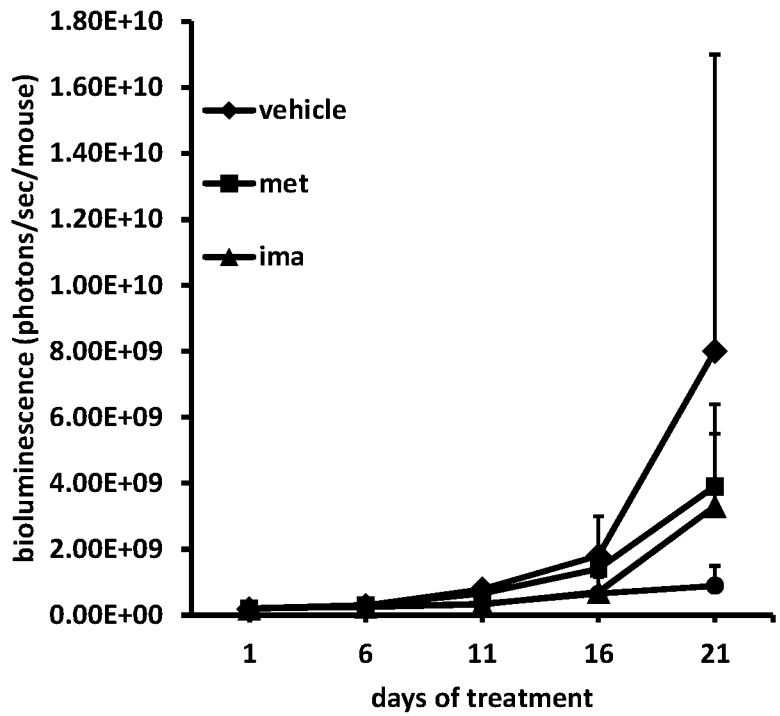
FIG. 3B is a plot of bioluminescence versus days of treatment of mice bearing TC-71 cell tumors. Treatments are as described in the legend for FIG. 3A above. Error bars represent standard deviation.

The results indicated that, in both the TC-32 and TC-71 xenograft mouse models, the combination of metformin and imatinib almost completely repressed tumor growth during the two-week-treatment. See FIGS. 3A and 3B. Furthermore, the tumors in these animals continued to grow significantly slower than the tumors in the mice in the single-drug groups or the vehicle group. See Id. No acute or chronic toxicity was observed for the drug combination.

At Day 21, mice were euthanized and the tumors were dissected to carry out pathological examination. Tumor tissues were stained for the presence of apoptotic cells using a terminal deoxynucleotidyl transferase dUTP nick end labeling (TUNEL) assay. Tumor section montage images were obtained with an ImageExpress automatic microscope under a 10× objective. The number of cells with TUNEL-positive staining was counted manually in a single-blinded fashion.

Figure 4A:
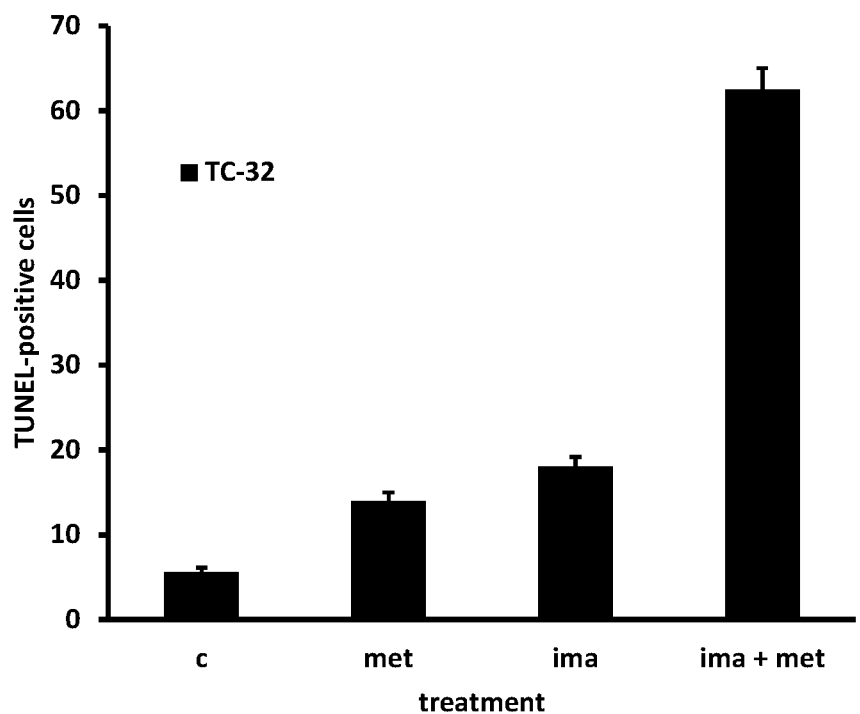
FIG. 4A is a bar graph showing the levels of apoptosis, represented by the number of terminal deoxynucleotidyl transferase dUTP nick end labeling (TUNEL)-positive cells, in tumor tissues obtained from mice bearing TC-32 cell tumors. The mice were treated as described in the legend for FIG. 3A above. Values are expressed as the number of TUNEL-positive cells per high power field. Error bars represent standard deviation.
Figure 4B:
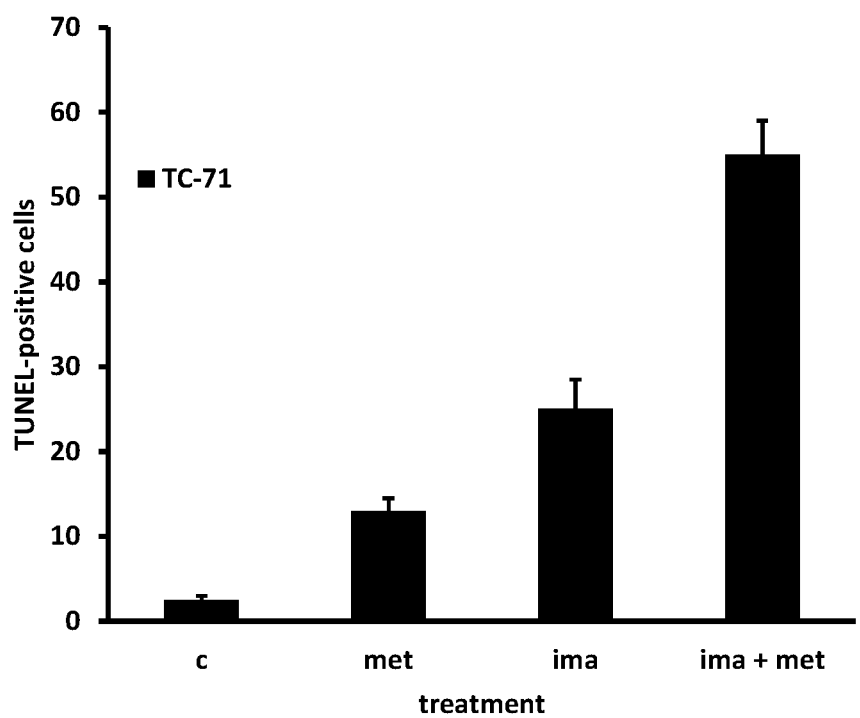
FIG. 4B is a bar graph showing the levels of apoptosis in tumor tissues obtained from mice bearing TC-71 cell tumors. The mice were treated as described in the legend for FIG. 3A above. Values are expressed as the number of TUNEL-positive cells per high power field. Error bars represent standard deviation.

The results show that administering a combination of imatinib and metformin led to a 3-5 fold higher number of apoptotic cells as compared to either drug alone in tumor tissue in both the TC-32 and TC-71 xenograft mouse models. See FIGS. 4A and 4B, respectively. For TC-32 cells, the number of TUNEL-positive cells seen after treatment with imatinib+metformin was significantly higher than control, metformin alone, and imatinib alone (p=0.002, p=0.031, and p=0.025, respectively). In TC-71 cells, the number of TUNEL-positive cells seen after treatment with imatinib+metformin was also significantly higher than control, metformin alone, and imatinib alone (p=0.002, p=0.006, and p=0.043, respectively).

Example 5: Gene Expression Profiling of Drug-Treated Tumor Cells

Gene expression in imatinib- and imatinib/metformin-treated TC-32 and TC-71 cells was examined using the Human DNA damage signaling pathway $RT^2$-PCR Array from SuperArray Bioscience Corporation (Frederick, Md. USA). The array detects expression of a panel of 84 genes related to DNA damage and DNA repair pathways. Housekeeping genes were included on the array to normalize RNA amounts. The resulting data was analyzed as previously described. See Rodriguez et al. 2010, Breast Cancer Res. Treat., 123(1):189-196.

Gene expression was examined in TC-32 cells and TC-71 cells treated for 12 h with imatinib or with imatinib plus metformin.

In TC-32 cells, the expression of 9 genes was significantly up-regulated by imatinib treatment and at the same time was repressed by the combination of imatinib and metformin. The 9 genes are DNA-Dependent Protein Kinase Catalytic Subunit (PRKDC), DNA Ligase 4 (LIG4), N-Methylpurine-DNA Glycosylase (MPG), Beta Cytoskeletal Actin (ACTB), DNA Glycosylase/AP Lyase Neil2 (NEIL2), DNA Mismatch Repair Protein (MLH1), Replication Protein A3 (RPA3), Ataxin 3 (ATXN3), DNA Excision Repair Protein ERCC-5 (ERCC5). These genes function as DNA repair genes and participate in two canonical repair pathways, i.e., DNA double-strand repair by non-homologous end joining (NHEJ) and DNA double-strand repair by homologous recombination (HR).

Turning to TC-71 cells, 11 genes were identified in these cells that were significantly up-regulated by imatinib and repressed by the combination of imatinib and metformin. The 11 genes are Nucleotide Excision Repair Homolog MMS19 (MMS19), LIG4, Beta-2-Microglobulin (B2M), Replication Factor C Activator 1 (RFC1), Poly ADP-Ribose Polymerase 2 (PARP2), Breast Cancer 2, Early Onset (BRCA2), Three Prime Repair Exonuclease 1 (TREX1), Xeroderma Pigmentosum Complementation Group C (XPC), UV Excision Repair Protein RAD23 Homolog A (RAD23A), A/G-Specific Adenine DNA Glycosylase (MUTYH), and APEX Nuclease Multifunctional DNA Repair Enzyme (APEX1). These genes are also enriched in the same two canonical pathways mentioned above, i.e., DNA double strand repair by NHEJ and HR.

Notably, LIG4, a gene essential for DNA double-strand break repair through NHEJ, was the only gene identified in both TC-32 cells and TC-71 cells that is upregulated by imatinib and suppressed by imatinib plus metformin.

Not to be bound by theory, these results suggest that the addition of metformin to cells inhibited DNA endogenous repair pathways that were elevated in response to imatinib-induced DNA damage. This combined effect of both drugs on inducing DNA damage and inhibiting DNA repair could explain the synergy of imatinib and metformin.

Example 6: Correlation of Elevated Gene Expression with Clinical Outcome

The clinical relevance of the 19 highly expressed genes identified in the $RT^2$-PCR array study described above in Example 5 was explored using the Ohali sarcoma dataset (Ohali et al. 2004, Oncogene, 23(55):8997-9006). The dataset contains gene expression information from 20 Ewing's sarcoma samples (14 primary-site tumors and 6 metastatic samples), as well as corresponding information regarding clinical outcomes. Clinical outcomes included death, metastasis, and recurrence. The results are shown in Table 3 below.

TABLE 3

Correlation of gene expression level with clinical outcome

| Gene | fold difference$^a$ | associated clinical outcome |
|---|---|---|
| ACTB | 3.881 | death |
| B2M | 4.347 | 5 year recurrence |
| MLH1 | 1.139 | metastasis |
| PRKDC | 3.576 | 5 year recurrence |
| XPC | 1.675 | 5 year recurrence |
| APEX1 | 2.396 | 5 year recurrence |
| ERCC5 | 1.561 | 3 year recurrence |
| MMS19 | 1.398 | 5 year recurrence |
| RAD23A | 1.570 | 3 year recurrence |

$^a$Fold difference in gene expression in poor outcome samples versus good outcome samples.

The results indicated that 9 out of the 19 genes examined were significantly upregulated in samples from patients having a poor prognosis as compared to samples from patients having a good prognosis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A method for treating a sarcoma, the method comprising administering to a subject having a sarcoma an effective amount of imatinib and metformin.

2. The method of claim 1, further comprising administering a tyrosine kinase inhibitor different from imatinib or a biguanide compound different from metformin.

3. The method of claim 1, further comprising administering a chemotherapy agent selected from the group consisting of cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, a topoisomerase inhibitor, and a combination thereof.

4. The method of claim 1, wherein the cancer is a Ewing Sarcoma family tumor.

5. A method for treating a Ewing family tumor, the method comprising:
obtaining a tissue sample from a Ewing family tumor in a subject;
determining in the sample a level of expression of a gene selected from ACTB, B2M, MLH1, PRKDC, XPC, APEX1, ERCC5, MMS19, and RAD23A; and
administering to the subject an effective amount of imatinib and metformin if the level of expression of the gene is elevated as compared to a predetermined level of expression of the gene.

6. The method of claim 5, further comprising administering a tyrosine kinase inhibitor different from imatinib or a biguanide compound different from metformin.

7. The method of claim 5, further comprising administering a chemotherapy agent selected from the group consisting of cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, a topoisomerase inhibitor, or a combination thereof.

8. The method of claim 5, wherein the determining step is carried out by quantitative reverse-transcription polymerase chain reaction.

* * * * *